(12) United States Patent
Dragan et al.

(10) Patent No.: US 7,942,669 B2
(45) Date of Patent: May 17, 2011

(54) GINGIVAL TISSUE RETRACTION DEVICE AND METHOD

(75) Inventors: William B. Dragan, Easton, CT (US); John J. Discko, Trumbull, CT (US)

(73) Assignee: Centrix, Inc., Shelton, CT (US)

( * ) Notice: Subject to any disclaimer, the term of this patent is extended or adjusted under 35 U.S.C. 154(b) by 759 days.

(21) Appl. No.: 11/825,802

(22) Filed: Jul. 9, 2007

(65) Prior Publication Data

US 2007/0259313 A1 Nov. 8, 2007

Related U.S. Application Data

(63) Continuation-in-part of application No. PCT/US2007/008232, filed on Mar. 30, 2007, which is a continuation-in-part of application No. 11/398,134, filed on Apr. 5, 2006, now Pat. No. 7,241,143, which is a continuation-in-part of application No. 11/139,912, filed on May 27, 2005, now Pat. No. 7,195,483, which is a continuation of application No. PCT/US03/37711, filed on Nov. 25, 2003, which is a continuation-in-part of application No. 10/307,695, filed on Dec. 2, 2002, now Pat. No. 6,890,177, application No. 11/825,802, which is a continuation-in-part of application No. 11/122,870, filed on May 5, 2005, now Pat. No. 7,189,075, which is a continuation of application No. 10/307,695, filed on Dec. 2, 2002, now Pat. No. 6,890,177.

(51) Int. Cl.
*A61C 5/14* (2006.01)

(52) U.S. Cl. ....................................................... 433/136

(58) Field of Classification Search .................... 433/34, 433/37, 38, 39, 136, 214
See application file for complete search history.

(56) References Cited

U.S. PATENT DOCUMENTS

| | | | |
|---|---|---|---|
| 2,396,203 A | 3/1946 | Robinson | |
| 2,620,502 A | 12/1952 | Russak | |
| 3,056,205 A | 10/1962 | Ennor | |
| 3,238,620 A | 3/1966 | Robertson | |
| 3,380,446 A | 4/1968 | Martin | |
| 3,705,585 A | 12/1972 | Saffro | 128/303.1 |
| 4,071,955 A | 2/1978 | Julius | 32/34 |
| 4,144,882 A | 3/1979 | Takemoto et al. | 128/172.1 |
| 4,173,219 A | 11/1979 | Lentine | 128/260 |
| 4,348,178 A | 9/1982 | Kurz | 433/6 |
| 4,468,202 A | 8/1984 | Cohen | 433/199 |
| 4,531,914 A | 7/1985 | Spinello | 433/136 |
| 4,543,063 A | 9/1985 | Cohen | 433/175 |
| 4,551,100 A | 11/1985 | Fischer | 433/218 |
| 4,617,950 A | 10/1986 | Porteous et al. | 132/91 |

(Continued)

*Primary Examiner* — Cris L Rodriguez
*Assistant Examiner* — Eric Rosen
(74) *Attorney, Agent, or Firm* — Fattibene and Fattibene LLP; Paul A. Fattibene

(57) ABSTRACT

A method and a device for effecting the cordless retraction of the gingival sulcus tissue that includes a dam shaped to be fitted onto a tooth. In one embodiment, the well of the dam is pre-filled with a predetermined amount of a flowable retraction material having a heavy viscosity or putty consistency. The preloaded tooth dam is fitted to a prepared tooth so that when pressure is applied onto the tooth dam, the retraction material is displaced under pressure and forced into the sulcus, causing the gingival tissue to retract away from the tooth to enlarge the gingival sulcus. In another embodiment the cap is filled with a dilatant material. In another embodiment, the cap is filled with an impregnated compressible porous material. In yet another embodiment, the cap is pre-dosed with an astringent or hemostatic agent.

9 Claims, 8 Drawing Sheets

U.S. PATENT DOCUMENTS

| | | | |
|---|---|---|---|
| 4,677,139 A | 6/1987 | Feinmann | 523/111 |
| 4,867,680 A | 9/1989 | Hare et al. | 433/37 |
| 4,961,706 A | 10/1990 | Jefferies | 433/39 |
| 5,190,457 A | 3/1993 | Schreinemakers | 433/214 |
| 5,213,498 A | 5/1993 | Pelerin | 433/37 |
| 5,362,495 A | 11/1994 | Lesage | 424/435 |
| 5,385,469 A | 1/1995 | Weissman | 433/40 |
| 5,639,445 A | 6/1997 | Curtis et al. | 424/49 |
| 5,676,543 A | 10/1997 | Dragan | 433/80 |
| 5,955,513 A | 9/1999 | Hare | 523/109 |
| 5,980,249 A | 11/1999 | Fontenot | 433/80 |
| 6,050,821 A | 4/2000 | Klaassen et al. | 433/214 |
| 6,155,262 A | 12/2000 | Thornton et al. | 128/859 |
| 6,375,461 B1 * | 4/2002 | Jensen et al. | 433/136 |
| 6,890,177 B2 | 5/2005 | Dragan | 433/136 |
| 7,189,075 B2 | 3/2007 | Dragan | 433/136 |
| 7,195,483 B2 | 3/2007 | Dragan | 433/136 |
| 7,241,143 B2 | 7/2007 | Discko, Jr. et al. | 433/136 |
| 7,328,706 B2 * | 2/2008 | Bardach et al. | 128/861 |
| 2003/0228339 A1 | 12/2003 | El-Nokaly et al. | 424/401 |
| 2004/0126740 A1 | 7/2004 | Coopersmith | 433/136 |
| 2004/0234926 A1 | 11/2004 | Halldin et al. | 433/173 |
| 2004/0265777 A1 | 12/2004 | Heasley | 433/136 |
| 2005/0069838 A1 | 3/2005 | Kollefrath et al. | 433/136 |
| 2005/0118552 A1 | 6/2005 | Coopersmith | 433/136 |
| 2005/0202367 A1 | 9/2005 | Kollefrath et al. | 433/136 |
| 2006/0063128 A1 | 3/2006 | Dragan | 433/89 |

* cited by examiner

GINGIVAL TISSUE RETRACTION DEVICE AND METHOD

RELATED APPLICATIONS

This application is a continuation in part of International application No. PCT/US 07/08232 filed Mar. 30, 2007, which is a continuation in part application of U.S. application Ser. No. 11/398,134 filed Apr. 5, 2006, now U.S. Pat. No. 7,241,143, which is a continuation in part application of U.S. application Ser. No. 11/139,912 filed May 27, 2005, now U.S. Pat. No. 7,195,483, which is a continuation of International Application No. PCT/US2003/037711 with an international filing date of Nov. 25, 2003, which is a continuation in part application of U.S. application Ser. No. 10/307,695 filed Dec. 2, 2002, now U.S. Pat. No. 6,890,177 B2, each of which is incorporated herein by reference.

This application is also a continuation-in-part application of U.S. application Ser. No. 11/122,870 filed May 5, 2005, now U.S. Pat. No. 7,189,075, which is a continuation of U.S. application Ser. No. 10/307,695 filed Dec. 2, 2002, now U.S. Pat. No. 6,890,177, which are both incorporated herein by reference.

FIELD OF THE INVENTION

This invention is directed to a method and device for effecting retraction of tissue, and more specifically to a method and device utilizing a dam pre-filled with a flowable retraction material for effecting the retraction of gingival tissue in preparing a tooth for the taking of an impression of the tooth necessary for making a crown or bridge dental prosthesis. In a more specific embodiment of the invention, the dam is provided with a retentive surface whereby the retraction material adheres to the retentive surface of the dam to facilitate the removal of substantially all of the retraction material from the retracted gingival tissue upon the removal of the dam.

BACKGROUND OF THE INVENTION

The traditional method for retracting gingival tissue prior to the taking of an impression of a prepared tooth to form a crown or bridge is to mechanically pack a small length of cord saturated with or without an astringent about the base of the tooth to enlarge the gingival sulcus space about the base of a tooth. After a period of time, the cord is removed from the enlarged space defined about the base of the tooth. Upon the removal of the cord, it frequently happens that coagulum formed to stop the bleeding or seepage of fluid is removed with the cord to result in the seepage of additional bleeding into the space. As a result, an impression cannot be made of the prepared tooth until the additional bleeding can be controlled or stopped. Thus, the traditional procedure for enlarging the space between the gum and the base of the tooth necessary for taking an accurate impression is tedious, time consuming and painful or extremely uncomfortable for the patient. Also, there exists the danger that the dentist may accidentally force the cord beyond the physiologic limit of the space to create a potential periodontal pocket which can cause the tooth to be eventually lost. The general practice of using the cord technique is relatively difficult and tedious for the dentist.

In the event that the space between the tooth and the gum that has to be retracted is very small, it becomes even more difficult for the dentist to place the cord without injuring the gum tissue and from forcing the cord beyond the physiologic limit, and renders the procedure more painful for the patient. Further, the placing of the cord is not a procedure which the dentist may delegate to a dental assistant or dental hygienist. Also, the packing of a retraction cord is a most disliked step to perform during a crown or bridge restoration procedure.

Efforts have been made to obviate the noted disadvantages of affecting the retraction of the gingival tissue by the use of a cord. One such known effort is the use of a kaolin type material that is mixed with an astringent salt which is simply placed about a prepared tooth to absorb the moisture to cause the gum tissue to shrink. Such a product is marketed by Sybron Dental Specialties under the brand name ExpaSyl.

It has been noted that such kaolin type material is packaged in a cartridge similar to a typical anesthetic cartridge commonly used in a dental office that requires the cartridge to be used with a syringe. The end of the cartridge is pierced with a needlelike cannula and the force of the syringing pressure is required to extrude the clay like kaolin material through the cannula. Because of the density of the kaolin type material, the cannula requires the opening to be very large so as to enable the kaolin type material to flow therethrough. The large gauge opening of the cannula renders the bending of the cannula difficult and which bending is often required in order to place the material in difficult to reach places within a patient's mouth. Because the opening of the cannula is quite large, difficulty is encountered in placing the kaolin type material about the gingival sulcus in a manner similar to the traditional method of packing cord to retract the gum tissue.

Also, the use of such kaolin type material to retract the gum tissue tends to crumble, rendering it difficult to place in the space between the gum tissue and the tooth to attain the desired retraction of the gum tissue. Another noted problem with such kaolin type material is the removal of the kaolin material after the period of time required to affect the hemostatic and the retraction. Generally, the kaolin material is required to be washed out using a water-air spray with extreme care to remove all the kaolin material without restarting any bleeding in the gingival sulcus.

Another known technique for effecting a non-cord retraction and/or hemostatic is disclosed in U.S. Pat. No. 5,676,543. Therein disclosed is a generally two part process utilizing two different viscosities of a silicone material to effect the cordless retraction and/or hemostatic of the gingival sulcus.

U.S. Pat. No. 6,890,177 discloses a more simplified cordless retraction method and device whereby the cordless retraction may be accomplished by resorting to a porous sponge or foam cellular dam which is shaped to conform with the prepared tooth or teeth, arranged to contain a two part silicone type impression material that includes a base portion and a catalyst, whereby the patient's biting force is utilized to apply the necessary pressure to effect the desired retraction.

Other devices and methods are used to retract the gingival sulcus e.g. Magic foam cord which is dependent upon an expanding silicone material which is a two-part, chemically cured component system that are required to be mixed by the dentist at chair side prior to application and which cures or sets to effect the retraction of the gingival tissue.

This invention is directed to an improvement to the non-cord retraction devices and procedures described hereinabove for effecting cordless retraction of the gingival tissue by utilizing a dam that has been preloaded with the retraction material.

SUMMARY OF THE INVENTION

An object of this invention is to provide a much simplified cordless retraction method and device for enlarging the gingival sulcus space between the gum tissue and the prepared tooth prior to the taking of an impression for making a crown or bridge.

Another object is to provide a dental dam capable of retaining the retraction material thereto for effecting ease of removal of the retraction material after effecting the cordless retraction and/or hemostatic of the gingival sulcus of a prepared tooth prior to the taking of an impression.

Another object is to provide for a hemostatic and/or cordless retraction of the gingival sulcus using the patient's own biting pressure to force the retraction material into the space between the gum tissue and the prepared tooth to enlarge the same.

Another object is to provide a cordless hemostatic and/or retraction method which is positive in operation and simple to perform.

Another object is to provide for a cordless hemostatic and/or retraction method of the gingival sulcus area, which is painless, comfortable and easy on the patient, and easy for the dentist to perform.

Another object is to provide a single step device and method to effect a gingival cordless retraction procedure.

Another object is to provide a dental dam initially preloaded with a predetermined amount of a flowable and pliable retraction material confined within the dental dam which can be readily fitted to a prepared tooth whereby cordless retraction of the gingival tissue is effected simply by the patient exerting a biting force on the dam.

Another object is to provide a dental dam formed of a retentive material that is pre-filled with a predetermined amount of a suitable, flowable, moldable or impression like retraction material whereby the moldable retraction material is cohesive and adheres or bonds to the retentive dam to facilitate a substantially complete removal of the material from the enlarged sulcus upon completing the cordless retraction of the gingival tissue.

Another object is to provide a single step method and device for retracting the gingival tissue by utilizing a retentive dam pre-filled with a flowable, cohesive and pliable moldable or impression-type retraction material.

Another object is to provide a single step method or device for retracting the gingival tissue utilizing a dam pre-filled with a retraction material fortified with an astringent and/or a hemostatic agent.

Another object is to provide a simplified device for effecting cordless retraction of the gingival tissue in the form of a light permeable dam preloaded with a light activated retraction, impression like material.

Another object is to provide a simplified device and method for effecting the cordless retraction of the gingival sulcus by the utilization of a dam preloaded with only the base portion of a two-part chemically cured impression like retraction material.

It is yet another object of the invention to provide a tissue retraction system that is pre-dosed with an astringent or hemostatic agent and therefore easy to use.

It is a feature of an embodiment of the invention that a non-setting material having dilatant properties is used within the cap or dam.

It is another feature of an embodiment of the present invention that a retraction material comprising polydimethylsiloxane, astringent or hemostatic agent, dilatant silicone, and a hydrophilic agent is used within the cap or dam.

It is another feature of an embodiment of the present invention that an impregnated compressible porous material is used within the cap or dam.

It is another feature of an embodiment of the invention a porous cap is pre-dosed with an astringent or hemostatic agent.

The foregoing objects and other features are attained by having a prepared tooth to be restored readied for the taking of an impression thereof in preparation of making a crown or bridge. After the tooth has been properly prepared and before a proper impression can be made, the gum tissue about the base of the tooth must be retracted to enlarge the gingival sulcus. In the event there is excessive bleeding, the bleeding can be controlled or stopped by the injection of a suitable astringent about the base of the tooth. Such astringent may include a hemostatic agent, e.g. aluminum chloride, ferric sulfate, ammonium aluminum sulfate and the like, applied to the cut tissue by syringing or other suitable applicators.

Where bleeding is slight or minimal, it may not be necessary to apply any astringent. After the controlled hemostatic, a dam having a well, groove or trough pre-filled with a predetermined amount of a retraction material, e.g. a silicone type impression material which may also be fortified with a hemostatic agent. A predetermined amount of the retraction or silicone impression material may also be optionally placed about the entire circumference of the prepared tooth at the gingival sulcus margin, preferably by syringing. The application of additional retraction material may also be optionally generously applied to cover the entire prepared tooth. The dam filled with the retraction or silicone impression material is then placed over the tooth, at which time the patient is instructed to apply a biting pressure onto the retention dam and to maintain the biting pressure thereon for a predetermined time period sufficient for the silicone material to set, e.g. 3 to 7 minutes. In one form of the invention, the well of the dam may be provided with a retentive surface to which the retraction material may adhere so that upon the removal of the dam, the retraction material adhered thereto may also be removed. Upon removal of the dam and retraction material, the tooth may be lightly washed and examined in preparation of the taking of the impression. If additional retraction of the gum tissue is required, the procedure may be repeated.

This invention further contemplates that the dam having a retentive surface may be formed of a natural or synthetic porous or cellular material, e.g. a cellular, porous or grooved plastic, or a fibrous material for defining a surface capable of retaining a retraction material bonded thereto. The fibrous material may be either natural and/or synthetic, e.g. woven or pressed cotton, rayon, nylon, linen and the like, formed in the shape of a cap or sleeve which is arranged to encircle the prepared tooth or teeth. Such cap or sleeve is preferably pre-filled with a suitable moldable or impression, putty-like retraction material, that is pliable, flowable and cohesive. When the cap or sleeve pre-filled with such moldable or impression-type material is fitted onto the prepared tooth and a biting pressure is applied onto the sleeve or cap, the flowable and pliable retraction material, which is confined within the cap or sleeve, is forced under pressure into the gingival sulcus to effect the retraction of the gingival tissue.

Due to the retentive nature or cellular structure of a retentive dam as described herein, when a biting force is applied onto the cap or sleeve, also causes the moldable retraction material to permeate into the cells, porosity, or grooves defining the retentive surface of the cap or sleeve to mechanically adhere or bond to the inner retention surface of the cap or sleeve. After the retraction of the gingival tissue has occurred, the retraction material adhered to the dam can be readily removed as the dam is removed, leaving the gingival sulcus free of any residual retraction material.

Retraction of the gingival tissue can be further enhanced by fortifying the moldable or impression-like retraction material with a suitable astringent/hemostatic agent.

DESCRIPTION OF THE PREFERRED EMBODIMENTS

Figure 1A:
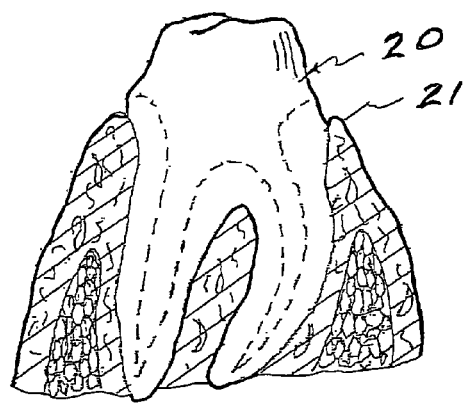
FIG. 1A is a side view of a prepared tooth prior to effecting the gingival retraction.

Referring to the drawings, there is shown in FIG. 1A a tooth 20 which has been prepared for receiving a crown or bridge, prior to effecting the retraction of the gingival sulcus 21. However, before the impression can be taken for preparing the crown or bridge, it is imperative that the gingival sulcus tissue 21 be retracted in order for the dentist to make an accurate impression of the prepared tooth 20.

Figure 1:
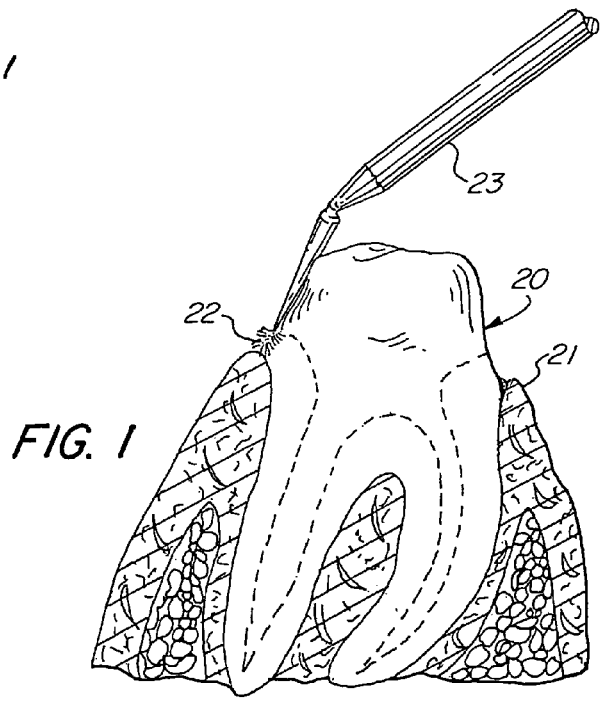
FIG. 1 is a side view of a prepared tooth and illustrating the placement of a hemostatic agent to control bleeding about the gingival sulcus area.

In accordance with this invention and to control any excessive gingival bleeding, an application of a liquid hemostatic agent 22, e.g. aluminum chloride, ferric sulfate or other suitable astringent is applied to the cut tissue in the area of the gingival sulcus. The astringent can be applied with Centrix's Benda micro applicator 23 as seen in FIG. 1, or by any other suitable applicator, e.g. Centrix, Inc.'s BENDA® brush, Soft-Stix™ disposable applicator, or syringe, and the like. The astringent 22 is applied with moderate pressure and by rubbing the astringent solution against the cut tissue to infuse the astringent solution into the cut capillaries. After the bleeding is under control, a dam 24 is adjusted and fitted to the prepared tooth 20 or to at least one tooth mesial and distal beyond the prepared tooth or teeth 20.

In accordance with this invention, the dam 24 is formed of a porous, cellular, foam, sponge like or rubber material which may be either natural or synthetic. The dam 24, as shown in FIG. 4, is formed for use on posterior teeth.

As shown, the dam 24 may be formed as an elongated block of a sponge, foam, rubber, or other type of porous, open or closed cellular material. It will be understood that the block of foam, sponge, porous or cellular material may be of any desired length from which the dentist may sever therefrom the desired length necessary to dam one or more teeth being worked upon. Conversely, the dam 24 may be pre-cut to size, depending upon the number of teeth that may require gum retraction and to which the finished crown or bridge is to be applied.

Figure 4:
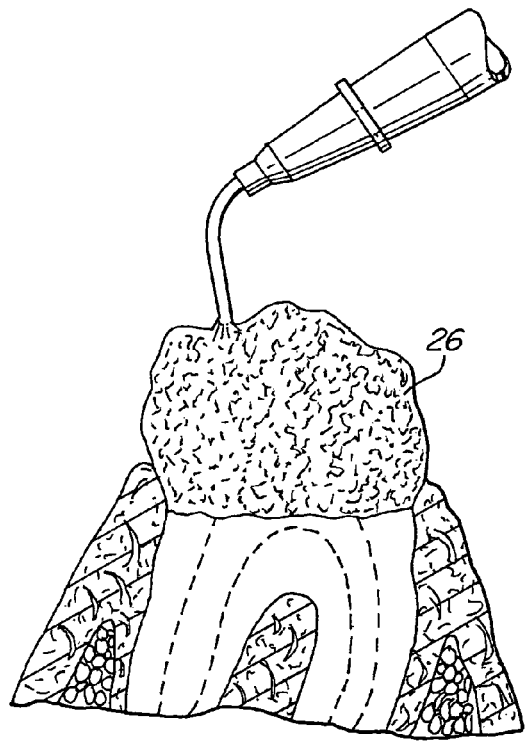
FIG. 4 illustrates a generous application of the retraction material covering the entire prepared tooth.

As seen in FIG. 4, the dam 24 is provided with a longitudinally U-shaped groove or trough 24A extending along the length thereof. The respective opposed side walls 24B and 24C and interconnected web or bottom 24D, as shown in FIG. 4, are sufficiently thick to contain a retraction material for exerting the necessary pressure to effect the gingival tissue retraction, as will be herein described.

Figure 7:
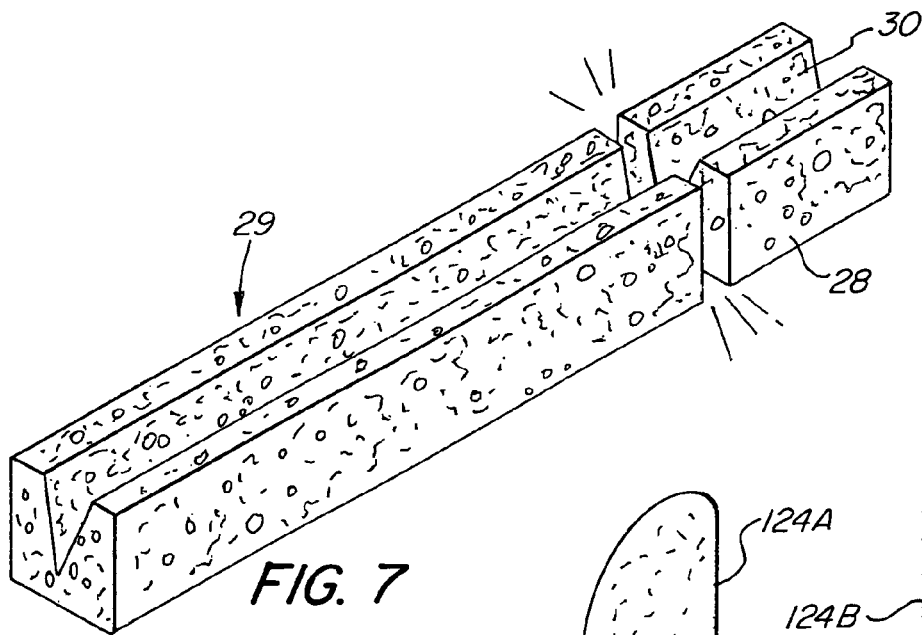
FIG. 7 illustrates a perspective view of a slightly modified sponge or foam dam for use in the cordless retraction of the gum tissue about anterior teeth.

FIG. 7 illustrates a modified block of sponge, foam, rubber, porous or cellular material from which a modified dam construction for use with anterior teeth is formed, as will be hereinafter described.

Figure 2:
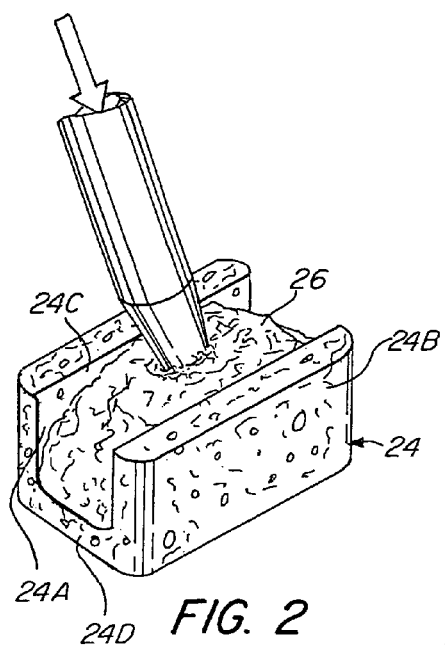
FIG. 2 illustrates the filling of the groove of a dam for use on posterior teeth with an amount of impression-like retraction material.

After the bleeding of the gum tissue to be retracted is controlled, the groove 24A of an appropriate size dam 24 is filled with a hereinbefore described silicone type impression-like retraction material 26, as shown in FIG. 2. The silicone type retraction material 26 may comprise a two-part composition which includes a base portion and a catalyst portion which, when mixed, will quickly set and become solid. The time of setting can be varied within a predetermined time range by controlling the ratio of catalyst to base. Such silicones are available from various manufacturers, e.g. CONQUEST by Pentron, EXAFLEX by G.C., EXTRUDE by Kerr Corporation or IMPRESS and EXPRESS by 3M Corporation. While the silicone retraction materials are preferred, dental materials such as polyethers, polysulfides, wax or other moldable materials may be used. The condensation silicone materials are preferred. The silicone material 26 may be also fortified with between five percent (5%) to twenty percent (20%) by weight of a suitable astringent to aid in the gum tissue retraction and hemostatic. Any of the known astringents may be used which are rendered compatible with the silicone. Some of the known astringents or hemostatic agents are aluminum potassium sulfate, aluminum sulfate, ferric sulfate, aluminum ammonium sulfate or alum, ferric chloride, aluminum chloride, sodium chloride, zinc chloride and others.

Figure 3:
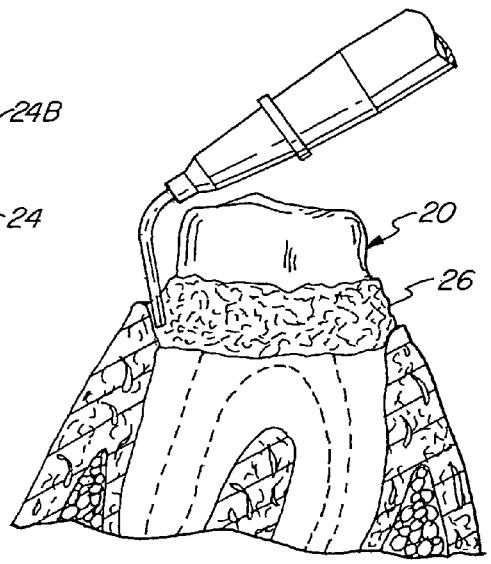
FIG. 3 illustrates an intermediate step of placing the retraction material about the gingival sulcus area.

The same silicone material may also be applied about the gingival sulcus area as shown in FIG. 3, preferably by syringing. The entire prepared tooth 20 may also be covered with the same silicone material as shown in FIG. 4. It will be understood that the step of applying the silicone material to the dam 24 or about the tooth as shown in FIGS. 3 and 4 can be reversed. With the tooth covered with the silicone material 26, and with the groove 24A of the dam 24 filled with the same silicone material, the silicone-filled dam 24 is placed onto the silicone covered tooth, as seen in FIG. 5.

Figure 6:
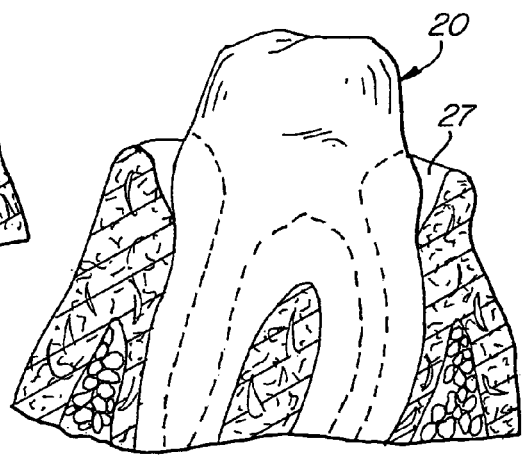
FIG. 6 is a view similar to that of FIG. 5 to illustrate the retraction and enlargement of the sulcus space between the retracted gum tissue and the base of the prepared tooth with the dam and impression material removed.
Figure 5:
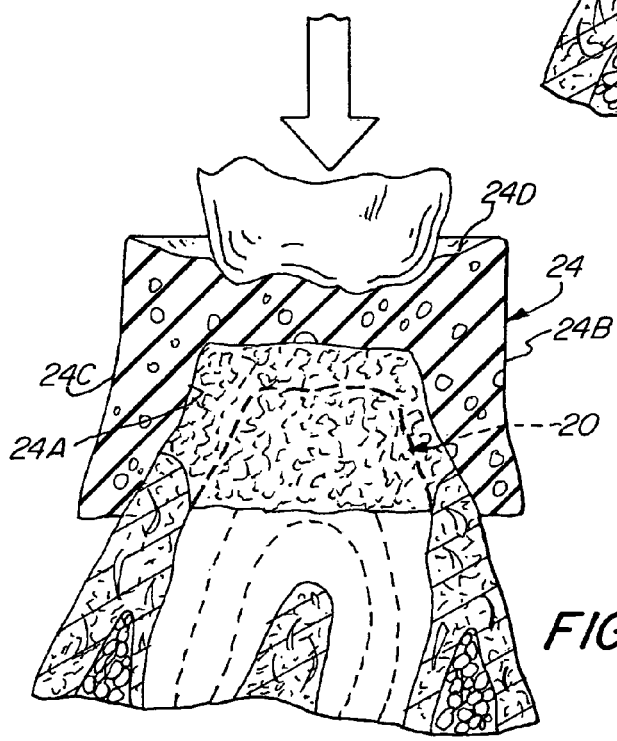
FIG. 5 illustrates the step of placing the filled sponge or foam dam onto the prepared tooth and the application of a biting pressure thereon.

With the filled dam 24 disposed over the silicone covered tooth or teeth, the patient is instructed to apply a biting force or pressure onto the dam 22 as shown in FIG. 5, and to maintain the biting pressure on the dam 24 until such time that the silicone material sets, approximately 3 to 7 minutes. Upon setting of the silicone material, the dam 24 and the set moldable material is removed to expose the prepared tooth as shown in FIG. 6. As the dam 24 is formed of a porous, cellular or foam sponge-like material, some of the silicone material will penetrate the retentive surface of the dam material, whereby the setting or curing of the silicone material causes the retraction material to mechanically adhere to the dam 24 so that the set retraction material can be removed in unison upon the removal of the dam 24. The tooth may then be lightly washed, dried and examined to determine if the gum tissue has been sufficiently retracted so as to enable an accurate impression to be made.

The bite pressure imparted by the patient onto the dam 24 as seen in FIG. 5, causes the silicone impression material to be forced into the gingival sulcus space, which together with the interaction of the astringent material causes the gum tissue in the gingival sulcus area to retract to enlarge the space 27 between the tooth and surrounding gum tissue as noted in FIG. 6. In the event additional retraction of the gum tissue is required, the procedure hereinabove described may be repeated.

While the porous, cellular, sponge or foam dams 24, as described herein, are preferred, it will be understood that other means may be used in lieu of the foam or sponge dams, e.g. rubber, silicone, plastic, a cotton roll or hollowed cotton gauze or pad, or other suitable material capable of containing the retraction material, when the biting pressure is applied and maintained. The use of the biting pressure on the dam 24 causes the silicone material, whether or not containing the astringent material, to be forced onto the gingival sulcus space, causing the gum tissue to be retracted an amount sufficient to permit an accurate tooth impression to be made for making a crown or bridge.

While the method described is in reference to retracting the gum tissue of a posterior tooth, the same method is applicable for retracting the gum tissue of an anterior tooth. However, for an anterior gum retraction, the dam is preferably constructed with a V-shaped groove, as in FIG. 7.

Referring to FIG. 7, an anterior dam 28 may be severed from an elongated block 29 of foam or sponge like material similar to that hereinbefore described, except the groove 30 is generally V-shaped as shown in FIG. 7. The opposed sides of the V-shaped groove 30 converge inwardly of the foam or sponge block. In all other respects, the construction of dam 28 and the use thereof is similar to that described with respect to the construction and use of dam 24. It will be understood that the foam material, from which the described dams are made, may be formed of open or closed cells, natural or synthetic porous, foam or sponge type materials.

However, when using closed cell foam or sponge material a retainer means may be needed to hold the retraction or silicone material within the dam to facilitate the removal of the retraction material with the dental dam upon completion of the gingival tissue retraction procedure.

Figure 8:
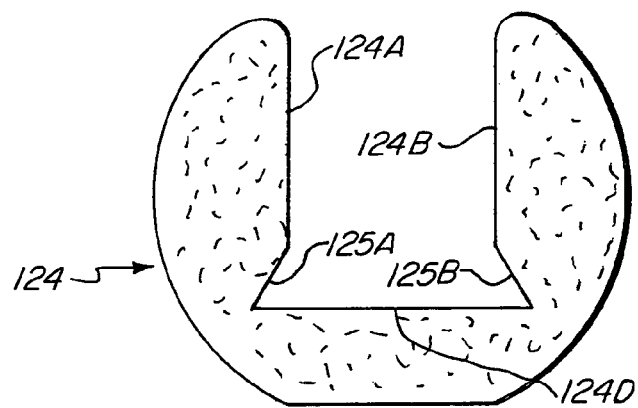
FIG. 8 is a cross-sectional view of another modification of a dental dam according to the present invention.
Figure 9:
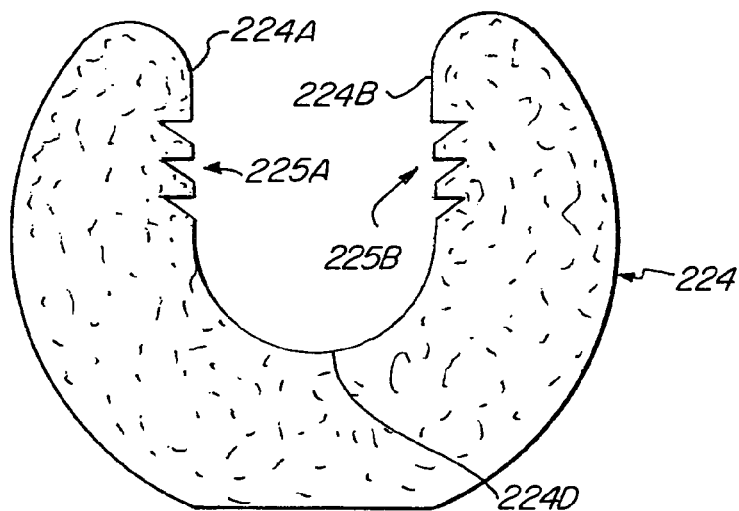
FIG. 9 is a cross-sectional view of still another embodiment of the dental dam according to the present invention.

FIGS. 8 and 9 illustrate dams having such a retainer means. In FIG. 8, the dam 124 has opposed side walls 124A and 124B interconnected by wall 124D. At the intersection of the side walls 124A and 124B and the bottom 124D are formed a retainer means in the form of undercuts 125A and 125B. The undercuts 125A and 125B help to retain the hardened, cured, or solidified silicone, retraction paste, or impression material within the dam 124 upon the removal of the dam 124 from the tooth being treated upon completion of the retraction procedure as herein described.

The undercuts 125A and 125B are particularly helpful when a closed cell, foam, sponge or molded part is used. A closed cell foam or sponge is advantageous because of its rigidity. However, the closed cell foam does not have open cells for adhering thereto the solidified silicone, retraction, or impression material, thus making removal of the retraction material difficult. In such event, the undercuts 125A, 125B provide the structure for effecting the bonding of the retraction material to the tooth cap for facilitating the removal of the retraction material together with the removal of the tooth cap, upon the completion of the retraction of the sulcus tissue.

FIG. 9 illustrates another embodiment of a dam 224 having a retainer means in the form of saw tooth shaped ridges 225A and 225B formed in side walls 224A and 224B, and which side walls are interconnected by a U-shaped bottom 224D.

The present invention may be sold in the form of a kit or package containing the required components to practice the retraction method of the present invention. For example, the kit or package may contain a liquid hemostatic or astringent agent and an applicator for applying it to the sulcus. The kit or package may also contain the silicone material, retraction, or the impression material that can set, and a dam. A delivery system may be included for use in applying a small quantity of the silicone-type retraction or impression material around the sulcus prior to the placement of the dam onto the tooth.

The method described and the dam for effecting the same are relatively simple, expedient and results in a positive retraction of the gum tissue so as to ensure that all margins can be captured in a subsequent impression procedure. The described invention further reduces the trauma and discomfort often encountered by the patient in a gum retraction procedure. Also, the present invention provides enhanced results with much greater ease on both the dentist and patient. The procedure is rendered so simple that it can be delegated to a dental assistant.

It has been noted that prosthodontics has become very important as people are having longer and healthier lives. As a result, prosthodontics has become an important part of dentistry that will enable people to keep their teeth longer, if not for their entire life span. A major part of prosthodontics involves the replacement or repair of broken down, decayed, endodontic or severely worn down teeth. A dentist can now repair or replace such teeth with crowns or bridges. A large portion of the crown and bridge dental work is the repair or restoration of a single tooth with an individual crown or, in lay terms, a "cap." It has been estimated that approximately 80% of all crowns and bridge work involves the repair of a single tooth. While the invention hereinafter described in reference to devices and methods of effecting cordless retraction of the gingival sulcus about a single tooth, it will be understood that the described invention, in apparent modified forms, may also be adapted for retracting the gingival sulcus about multiple adjacent teeth.

The device and/or method to be hereinafter described is such that the cordless retraction of the gingival sulcus of a tooth or teeth can be accomplished in a single step, as distinguished from those methods or devices that requires a chemically curing retraction material consisting of multiple components that include a base portion and a catalyst portion that require mixing by the dentist at chairside prior to use. The single step method or device as used herein means a tooth cap or dam which is initially preloaded with a moldable retraction material which is designed to fit onto a tooth without requiring the dentist to mix and/or pack the retraction material in the dam prior to the tissue retraction procedure.

Figure 10:
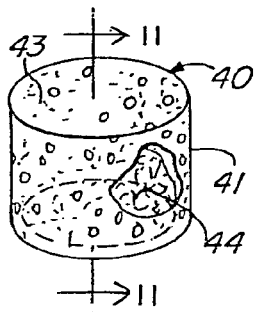
FIG. 10 is a perspective view of another modified form of the invention having portions broken away.

As shown in FIG. 10, the tooth cap or dam 40 is designed and shaped so as to be fitted onto a single tooth 20 which is the subject of the restoration. In the illustrated embodiment, the tooth cap or dam 40 includes a peripheral wall 41 which is formed of a porous or cellular material, formed either of plastic or of natural or synthetic fibers, e.g. cotton, nylon, rayon and the like, which can be molded, woven, pressed or rolled so as to define a well or hollow 42 within the peripheral wall 41 of the tooth cap or dam 40. One end of the tooth cap or dam 40 is closed by an end wall 43. Preferably, the closing end wall 43 is formed of the same material that makes up the peripheral wall 41. It will be understood that material from which the tooth cap or dam 40 is formed must be sufficiently rigid and have a limited amount of elasticity so as to function as a dam for containing, confining and directing the retraction material 44 disposed therein toward the gingival sulcus when the tooth cap or dam 40 is used to effect a cordless retraction of the gingival sulcus. As shown, the interior surfaces of the well or hollow 42 are laced with minute pores, cells or voids, due to the nature of the material forming the tooth cap 40.

In accordance with this invention, the well or hollow 42 formed within the peripheral wall 41 is pre-filled with either a setting or non-setting retraction material 44 that initially has a putty consistency, e.g. silicone, wax, acrylic or like material that has both flowable and cohesive qualities that will not tear or break apart when removing the tooth cap or dam 40 from the tooth upon completion of a gingival sulcus retraction procedure. The retraction material must be of sufficient density so as to be capable of exerting the required pressure necessary to effect the separation of the gingival tissue from the base of the tooth when a biting pressure is applied onto the tooth cap or dam 40 during a retraction procedure.

The retraction material 44 may comprise a light curable impression material such as methylmerthaculate or a light curable silicone. Other materials suitable for effecting cordless retraction of the gingival sulcus include silicone, microcrystalline wax or other similar substances such as a "pillow soft" silicone made by McKeon Products or other manufacture, such as Dow Chemical.

The hollow or well 42 of the tooth cap 40 may also be pre-loaded with only the base portion of a chemically cured impression-like, retraction material. Such base portion of the chemically cured impression-like, retraction material will normally not set until treated or mixed with the appropriate catalyst.

Preferably, the consistency of the base portion of the chemically cured impression material should be akin to that of moldable putty. Pre-loading only the base portion of a chemically cured impression material into the well or hollow portion 42 of the tooth cap or dam 40 will not set or cure over time. The "base component" of a chemically cured impression material as used herein means that component or components of an impression material that is free of any catalyst that would cause the base portion or component to set or cure, i.e. harden.

"Pre-filled" or "pre-loaded" as used herein is defined as having the retraction material placed into the tooth cap 40 or sleeve 60 in a factory or assembly facility so that the pre-filled tooth cap or sleeve is marketed or supplied to the dentist in a completely fabricated condition so that the "pre-filled" tooth cap can be used by the dentist without requiring the dentist to mix or pack the retraction material into a dam at chair side.

The advantage which the pre-filled tooth cap 40 has over the prior known methods of effecting cordless retraction is that the retraction of the gingival tissue can be effected in a more efficient and time-saving one-step procedure.

Figure 12:
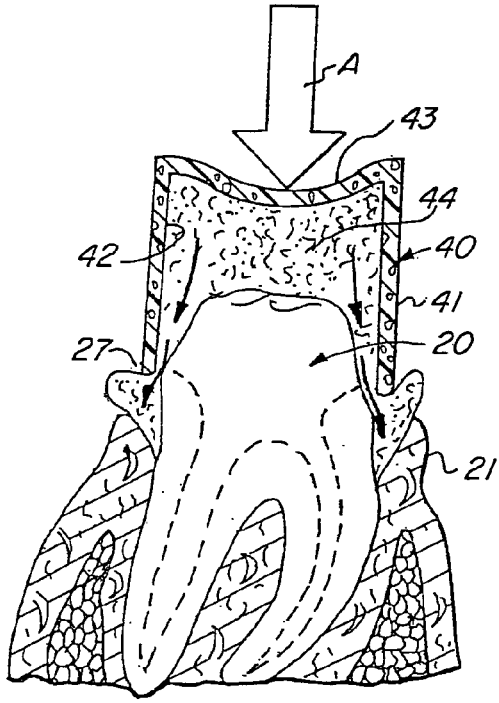
FIG. 12 is a side section view of the embodiment of FIG. 10 as applied to a prepared tooth to illustrate the retraction of the gingival sulcus tissue.

As indicated in FIG. 12, to effect the cordless retraction of the gingival tissue, the dentist need only place a pre-filled dental dam 40, as shown in FIG. 12, onto the tooth 20 to be restored and requesting the patient to impart a biting pressure onto the closed end 43 of the tooth cap or dam 40. As indicated by arrow A, the biting pressure imparted onto the closed end 43 of the tooth cap 40 will cause the closed end 43 to deform as shown, causing the confined moldable retraction material 44 to flow and exert a pressure about the entire base of the tooth whereby the gingival sulcus tissue 21 retracts away from the tooth 20. The exerted pressure forces the retraction material 44 between the tooth 20 and the gingival tissue 21 to enlarge the sulcus 27 about the entire base line of the tooth, as best seen in FIG. 12. In doing so, the retraction material 44 is also forced into the pores, cells or retentive surfaces of the interior wall of the tooth cap 40 to form a mechanical bond with the interior wall surface that defines the hollow or well 42.

The pressure imparted onto the tooth cap or dam 40, as shown in FIG. 12, is maintained for a predetermined period of time, e.g. 3 to 7 minutes, depending upon the amount of bleeding or oozing that may be occurring. As the applied pressure also causes the retraction material 44 to flow into the pores, cells or retaining means formed on the interior surfaces of the well or hollow 42, the retraction material becomes bonded to interior wall of the cap 40, which assures that the retraction material can be totally moved as the tooth cap 40 is released and removed from the tooth, to result in an enlarged sulcus substantially free of any residual retraction material 44. Thus, a dentist need not be required to physically remove any residual retraction material from the sulcus space 27 upon completion of the sulcus retraction procedure. As a result, any possibility of injuring the delicate gingival tissue and restarting the bleeding which may occur in effecting the removal of residual material from the enlarged sulcus is avoided.

If desired, a hemostatic and/or astringent agent may be incorporated in the retraction material, as hereinbefore noted.

The retraction method now becomes a simple one step procedure. After a tooth has been properly prepared for a crown or bridge, a properly sized tooth cap 40, pre-loaded with a suitable retraction material as herein described, is placed onto the prepared tooth 20, and the patient is instructed to bite down on the tooth cap 40 and hold the biting pressure for 3 to 7 minutes. Upon the expiration of said predetermined time interval, the patient releases the biting pressure, to permit the dentist to effect the removal of the tooth cap 40. In doing so, the retraction material when bonded to the walls of the hollow or well 42 is also removed, leaving behind a clean space or sulcus about the tooth 20 formed by the retraction of the gingival tissue 21. Thus, the time and trauma to the patient is substantially reduced.

Figure 13:
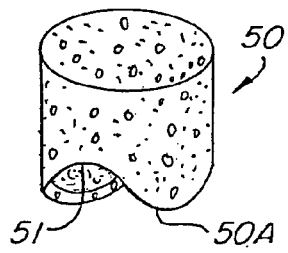
FIG. 13 is a perspective view of another embodiment of the invention.

FIG. 13 illustrates a modified form of a pre-filled tooth cap 50 embodying the invention. The tooth cap 50 is similar to tooth cap 40, except that tooth cap 50, adjacent the open end 50A, is provided with a transverse notch or cutout portion 51 which permits the notch or cutout portion on opposite sides of the tooth cap 50 to complement or conform to the curvature of the gum line between adjacent teeth. In all other respects, the structure and method of use of tooth cap 50 is similar to that describe with respect to tooth cap 40.

Figure 14:
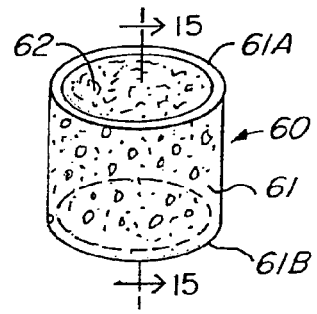
FIG. 14 is a perspective view of still another embodiment of the invention.
Figure 11:
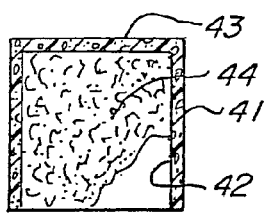
FIG. 11 is a section view taken along section line 11-11 on FIG. 10.
Figure 15:
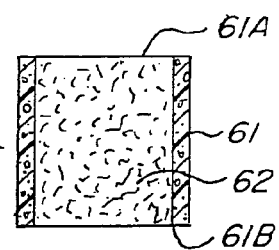
FIG. 15 is a section view taken along line 15-15 on FIG. 14.

FIGS. 14 and 15 illustrate a further embodiment of a tooth cap. As shown in FIGS. 14 and 15, the tooth cap 60 is formed of a material similar to that hereinbefore described, configured in the shape of a cylinder 61 which is opened at the opposed ends 61A, 61B. The cylinder 61 is preloaded with a retraction material 62 as hereinbefore described. If desired, it will be understood that one open end 61A or 61B of cylinder 61 may be provided with a transverse notch or cutout portion similar to notch 51 of FIG. 13.

Figure 17:
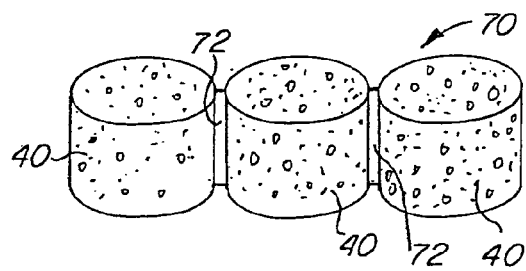
FIG. 17 is a perspective view of a series of frangibly connected preloaded dams embodying the present invention.
Figure 19:
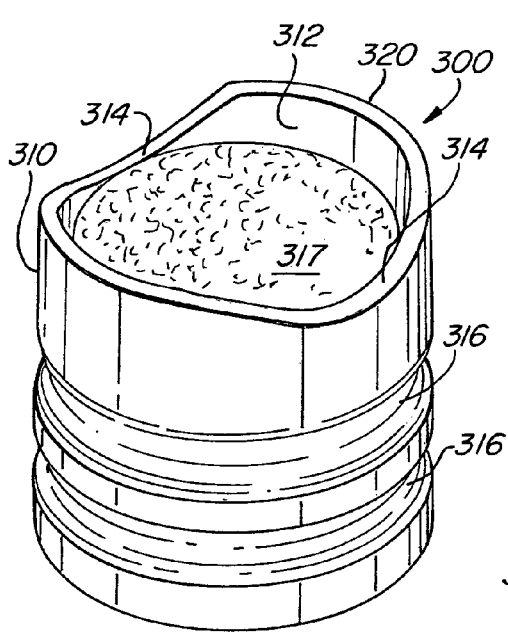
FIG. 19 is a perspective view illustrating another embodiment of the present invention.

If desired, the tooth caps described herein, e.g. tooth caps 40, 50, 60, or 80 may be formed in a chain or tree 70 having a frangible web or tear-line 72 connecting a series of adjacent tooth caps to one another as indicated in FIG. 17. The arrangement is such that a dentist can readily separate an individual tooth cap 40 from its chain or tree 70 along the frangible tear-line 72 as needed.

Figure 18:
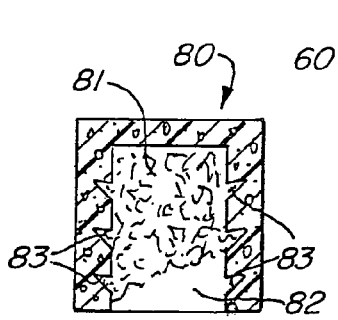
FIG. 18 is a section view of a modified form of a pre-loaded dental dam.

FIG. 18 illustrates another modified form of the invention. The tooth cap 80 of FIG. 18 is similar to that hereinbefore described except that the interior surfaces 81 that define the boundaries of the well or hollow 82 are provided with a series of undercuts or notches 83 to provide retention means to enhance the bonding or adhesive of the retraction material 81 to the interior surfaces of the tooth cap 80.

It will be understood that the tooth caps described herein may be made in different sizes and/or shapes to accommodate the size or shape of the tooth being restored.

The foregoing method may be practiced by using a retraction material, e.g. a non-curing silicone putty material or an equivalent thereof having a heavy viscosity preloaded in any of the described tooth caps 40, 50, 60 or 80, as shown in the drawings. In the event any excessive bleeding or oozing is encountered, an astringent/hemostatic agent can be burnished into the gingival sulcus before the pre-loaded compressible tooth cap is placed over the tooth. The maintaining of the biting force of the patient onto the tooth cap described herein for the predetermined time period, e.g. 3 to 7 minutes, should stop any bleeding, retract the gingival tissue, and widen the gingival sulcus 27, preparatory to the taking of an impression for the fabrication of the appropriate crown or bridge.

In the event the retraction material preloaded into a cap 40, 50, 60 or 80 as herein described is a light curable impression type material, it will be understood that such dental dam be formed of either a transparent or light pervious material so as to permit the curing light beam to penetrate therethrough to set or cure the light curable retraction material contained therein.

Figure 16:
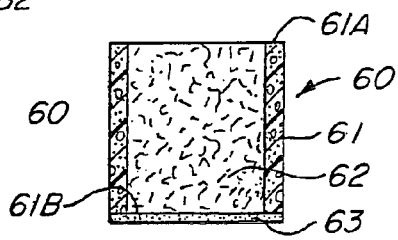
FIG. 16 is a section view of another modified form of the invention.

In the event that the base portion only of a two-part chemically cured impression or retraction material is preloaded in the described dental dam dams 40, 50, 60, or 80, the dentist, prior to placing the preloaded cap onto the tooth, may apply a thin layer 63 of a catalyst onto the exposed surface of the base material 62, as shown in FIG. 16, so that the exposed portion of the retraction material 62, in contact with the catalyst layer 63, may cure upon a lapse of a predetermined time interval, e.g. 3 to 7 minutes.

Preloading a tooth cap with a retraction material capable of either setting or curing or non-setting enhances both the enlarging of the sulcus and the maintaining of the enlarged sulcus to insure the making of a proper impression of the tooth as well as enhancing and assuring that substantially all of the retraction material is moved from the sulcus with the removal of the tooth cap.

FIGS. 19-23 illustrate another embodiment of the present invention. In this embodiment, a unique unit pre-dosed gingival retraction system 300 is disclosed. A cap or dam 310 has a generally cylindrical configuration. The wall 312 has opposing cut out portions 314 forming a scalloped edge. Adjacent each scalloped edge or cut out portion 314 is a full height edge portion 320. External grooves 316 circumscribe a lower portion of the cap 310. The grooves 316 permit easy handling, provide a place on which to attach a retaining string, not shown, and provide some compression compliance to the cap 310. Non-setting putty like material 319 is placed within the cap 310.

Figure 20:
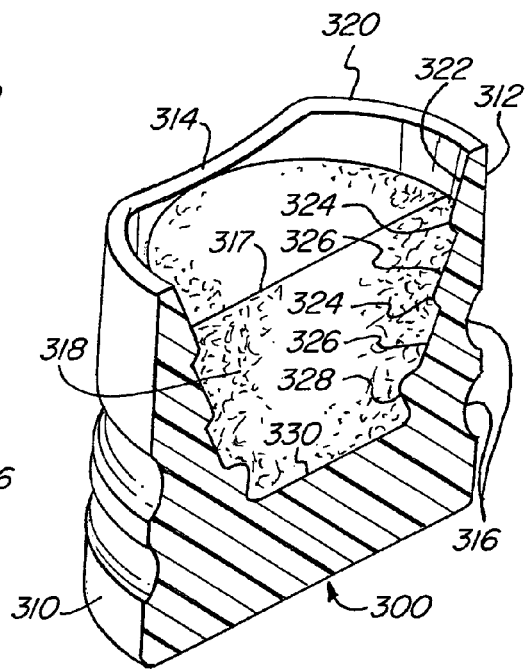
FIG. 20 is a cross section of the embodiment of the invention illustrated in FIG. 19.
Figure 21:
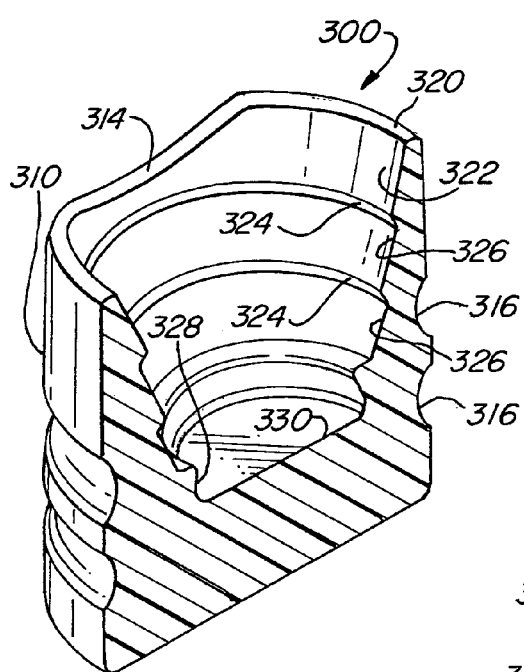
FIG. 21 is a cross section of the embodiment of the invention illustrated in FIG. 19 without any material.

FIGS. 20 and 21 illustrate in more detail the internal construction or configuration of the cap 310. Formed within the interior of the cap 310 are a plurality of ridges 324 and slanted walls 326. Adjacent the open end of the cap 310, a tapered rim or edge 322 is formed. Adjacent the bottom closed end 330 of cap 310 is a bottom ridge 328 that forms a greater overhang or reduced diameter section than that of the ridges 324.

Figure 22:
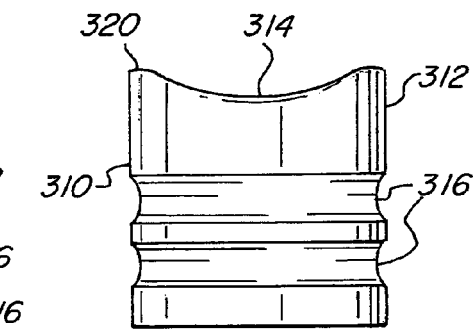
FIG. 22 is an elevation view of the embodiment of the invention illustrated in FIG. 19.
Figure 23:
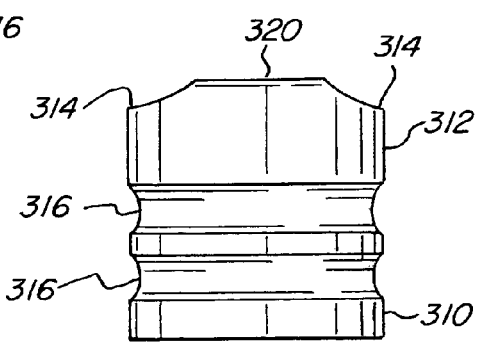
FIG. 23 is an elevation a view of the embodiment of the invention illustrated in FIG. 22 turned ninety degrees.

FIGS. 22 and 23 more clearly illustrate the scalloped edge or cut out portion 314 and the full height edge portion 320 along the open end of the cap 310. The scalloped edges or cut out portions 314 and the tapered rim or edge 322 aids in positioning the cap 310 within the mouth of a patient and permits easier placement between adjacent teeth.

The cap 310 is preferably made of a flexible soft material such as a styrenic block copolymer material. One suitable material is sold under the trademark DYNAFLEX by GLS Corporation located in McHenry, Ill., US.

The non-setting material 318 placed within the cap 310 has the properties of providing sufficient flowability, yet sufficient resistance to pressure so as to fill the sulcus between the tooth and the gum line resulting in effective and clean retraction of the gums. The material must also have the properties of sufficient adhesion to the cap 310 so as to permit removal of the cap 310 together with the material 318 remaining intact therein. The ridges 324 and bottom ridge 328 greatly facilitate the retention of the material 318 within the cap 310. The material 318 is preferably a dilatant material. A dilatant material is a shear thickening fluid, which is one in which viscosity increases with the rate of shear. A dilatant material may also be a non-Newtonian fluid. Additionally, a dilatant material may have the ability to increase in volume when its shape is changed. The dilatant material has flow characteristics that are desirable, and initially resist flow. The table below illustrates the preferred general formula for the material 318 placed within the cap 310.

| PERCENT BY WEIGHT | MATERIAL |
| --- | --- |
| 10 to 30% | Polydimethylsiloxane |
| 9 to 20% | Astringent or hemostatic agent, such as aluminum chloride, aluminum potassium sulfate, aluminum sulfate, alum, or ferric sulfate, or other known retraction |

-continued

| PERCENT BY WEIGHT | MATERIAL |
|---|---|
| | agents that have hemostatic and astringent properties, or an astringent that also has hemostatic properties |
| 1 to 10% | Silicone oil |
| 1 to 75% | Dilatant silicone |
| 5 to 20% | Potassium polyacrylate |

In a preferred formulation, the non-setting material 318 comprises 30% polydimethylsiloxane; 9 to 10% hemostatic or astringent agent such as alum, aluminum sulfate, aluminum chloride, ferric sulfate; 1 to 2% silicone oil; 58 to 68% dilatant silicone; and 10% potassium polyacrylate. In yet another preferred formulation, the non-setting material 318 comprises approximately 15% polydimethylsiloxane, 10% astringent or hemostatic agent, 1% silicone oil, 74% dilatant silicone, and 10% potassium polyacrylate. In yet another preferred embodiment, the non-setting material 318 comprises 63 to 68% polydimethylsiloxane, 10% astringent or hemostatic agent, 2% silicone oil, 10% dilatant silicone, and 5 to 10% potassium polyacrylate. Hemostatic or astringent agents such as aluminum potassium sulfate, ammonium alum, ammonium alum dodecahydrate, as well as others may be used. Additionally, potassium polyacrylate is a hydrophilic material that absorbs water. Other hydrophilic materials may be used, such as sodium polyacrylate or other polyelectrolytes.

A non-setting material of the above identified formulation has been found to have advantageous properties in permitting the cap 310 to be pre-filled with the non-setting material that is relatively stable and can be prepackaged for easy use by a dentist. The non-setting material resists excessive flow and yet conforms to the gum line so as to provide effective retraction of the gum tissue away from the tooth with a minimum of effort and discomfort. Therefore, the present invention provides an easy, simple to use device that is convenient for the dentist, making dentistry easier.

After filling the cap 310 with the non-setting material 318, the material 318 may be dusted with a powder material 317 comprising approximately 75% polyacrylate and 25% of an astringent agent such as alum, or its equivalent.

Figure 24:
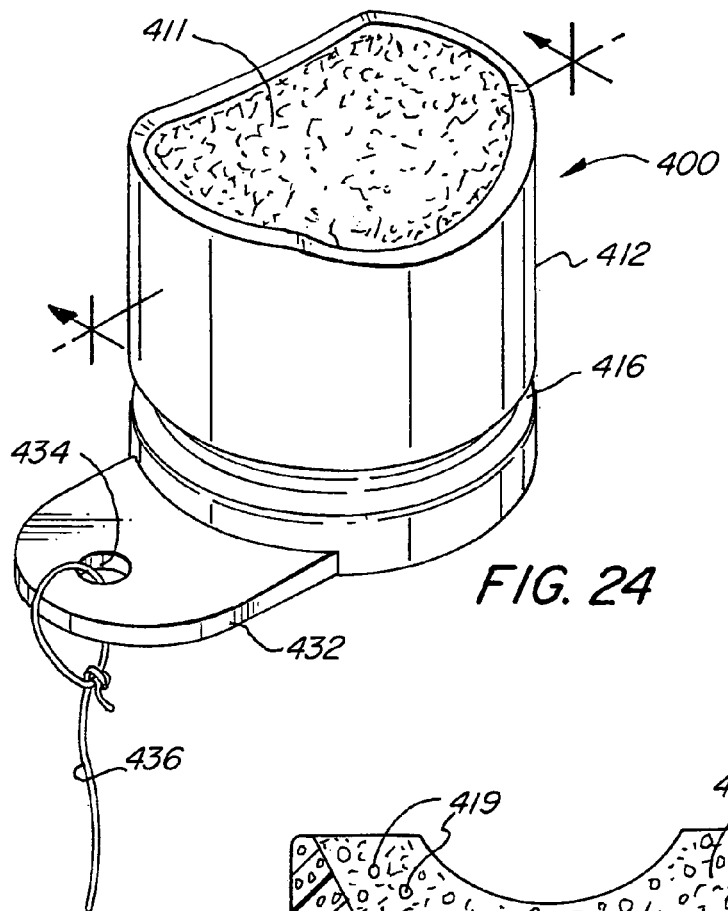
FIG. 24 is a perspective view of another embodiment of the presenting invention.
Figure 25:
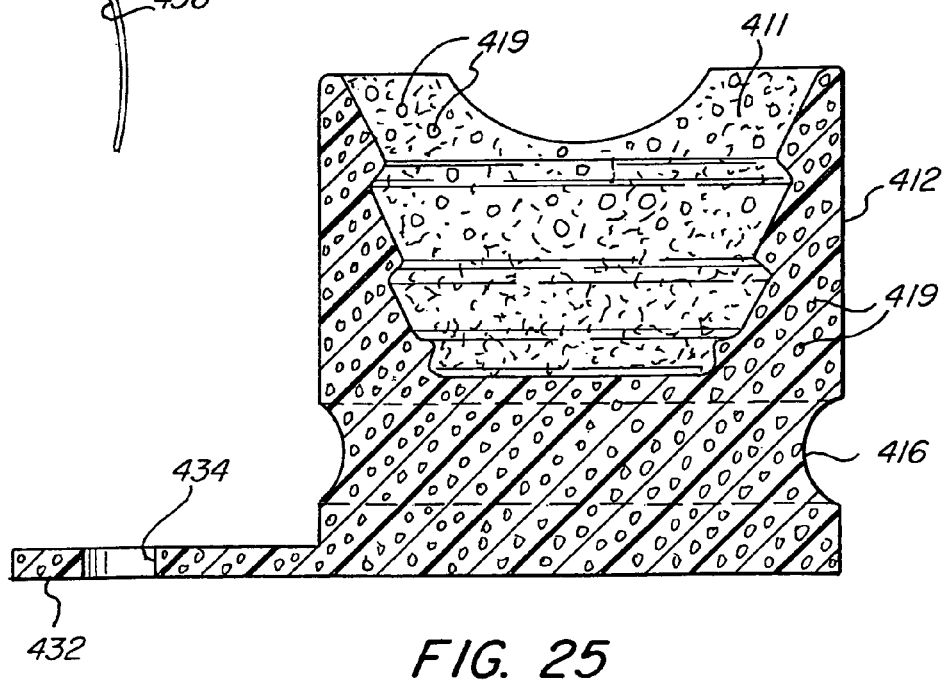
FIG. 25 is a cross section of the embodiment of the invention illustrated in FIG. 24.

FIGS. 24 and 25 illustrate another embodiment of the invention. In this embodiment, a unit dose retraction system having a safety tab and made of a porous material 400 is illustrated. The retraction system 400 comprises a cylindrical wall 412 made of a porous material. Within the cylindrical wall 412 is placed a softer or more compressible porous material 411. The cylindrical wall 412 is less compressible than the porous material 411. On an exterior surface of the wall 412 is a groove 416. At the bottom of the wall 412 is a safety tab 432 having a hole 434 therein. A string or cord 436 may be conveniently tied to the tab 432 as a safety feature in the event a patient inadvertently swallows the retraction system 400. The wall 412 is made of a porous material that contains a retraction agent which may be or include an astringent or hemostatic agent 419 impregnated therein. The softer foam or compressible porous material 411 is placed within the cylindrical wall 412 and may also be impregnated with a retraction agent which may be or include an astringent or hemostatic agent 419. In this embodiment, the astringent or hemostatic agent 419 may be dried and reactivated upon applying moisture. In The moisture may be applied either prior to placement in a patient's mouth, or by being activated by the patient's saliva. In another embodiment the softer foam or compressible porous material 411 may be impregnated with a dilatant non-setting material. The dilatant non-setting material may be of a formula similar to that described above for the material 318 illustrated in FIG. 20. The combination of the compressible porous material and the dilatant non-setting material has been found to work particularly well in retracting gum tissue. It is believed that the combination of pressure and retraction agent facilitates the retraction of the gum tissue. The compressible porous material 411 may also aid in absorbing excess fluid that may form around the teeth in the mouth. The porous material making up the walls 412 is preferably more rigid than the porous material or foam 411 contained therein. The softer porous material 411 conforms around the tooth and applies pressure to the gingival sulcus, aiding in retraction of the gum. In this embodiment of the present invention, the combination of porous materials facilitate application of a hemostatic or astringent agent together with the ability to absorb excess fluids, such as blood, that results in good retraction permitting the taking of a better impression.

Figure 26:
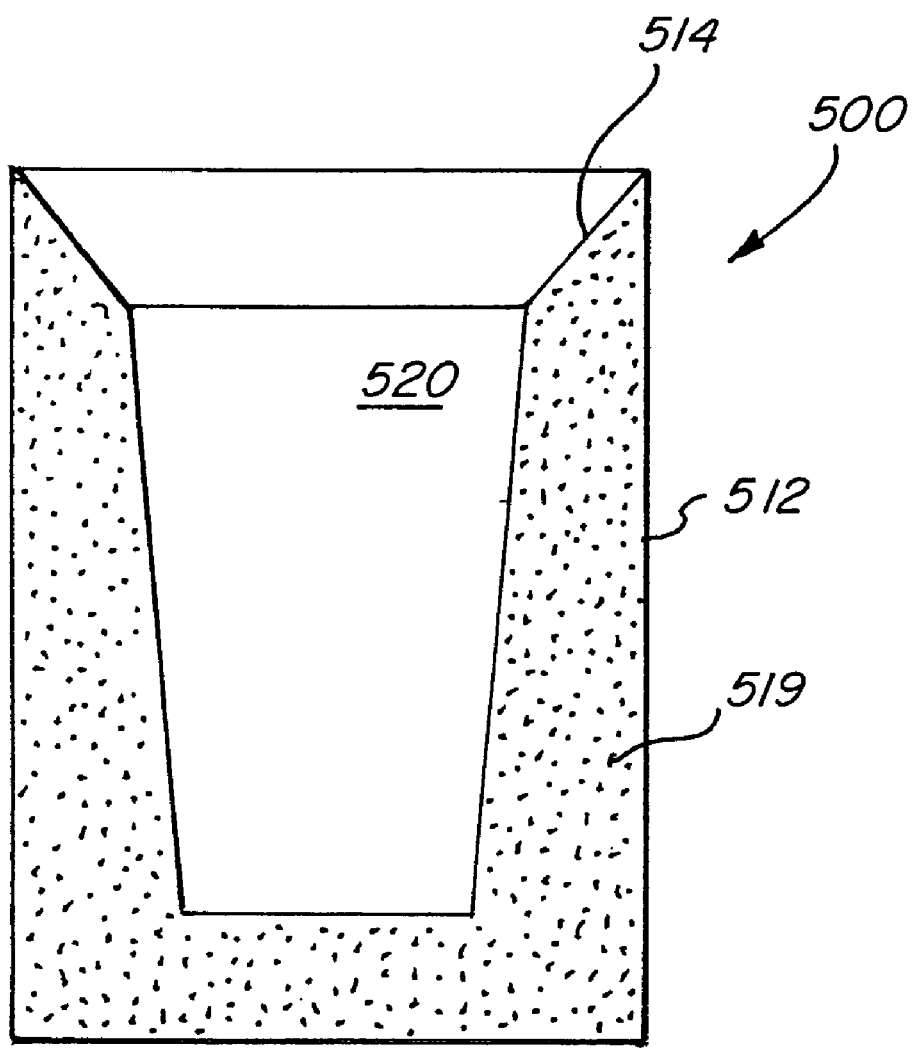
FIG. 26 is a cross section schematically illustrating another embodiment of the invention.
Figure 27:
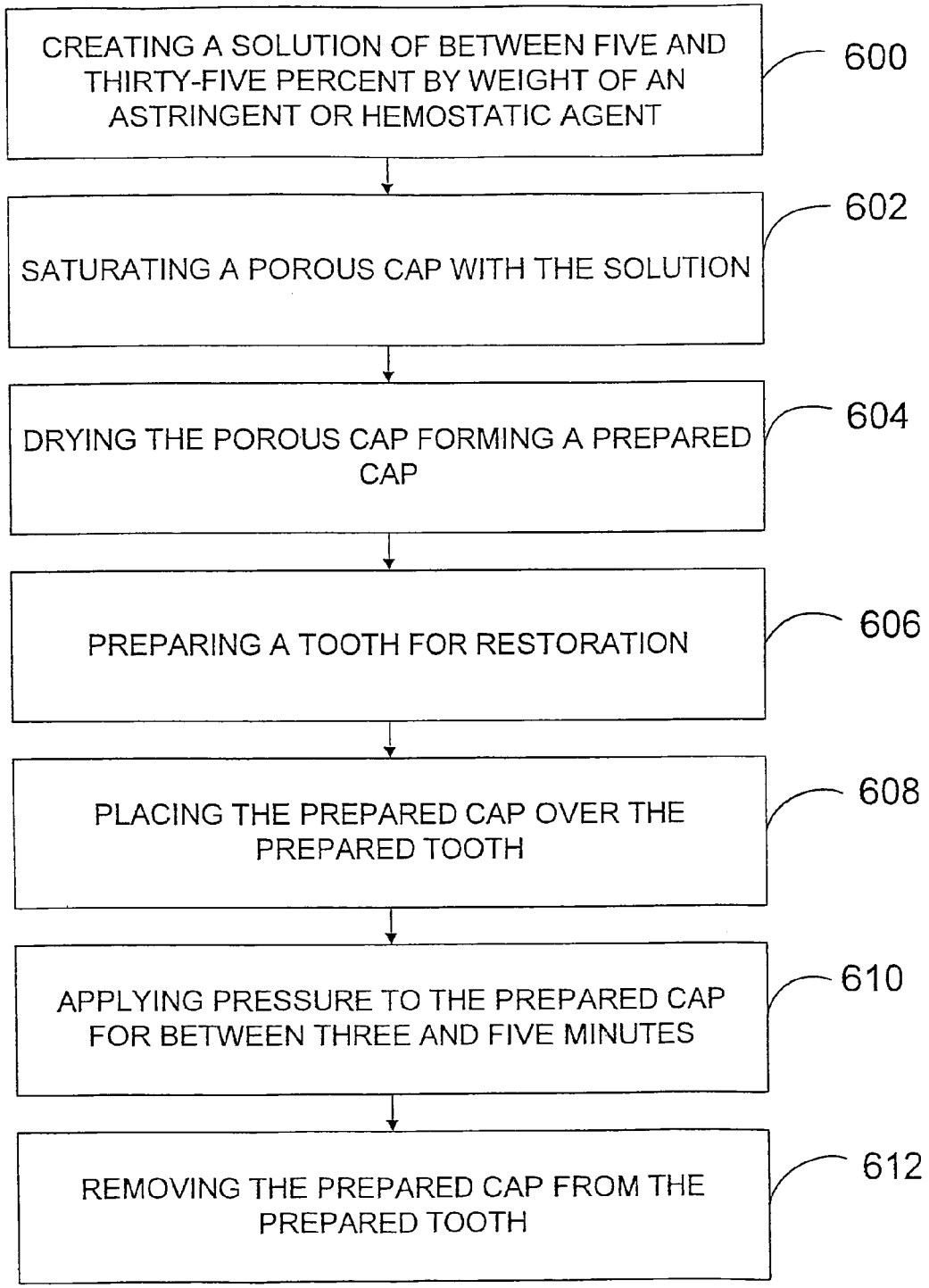
FIG. 27 is a block diagram illustrating the method steps of practicing an embodiment of the invention.

Another embodiment of the invention is illustrated in FIGS. 26 and 27. FIG. 26 illustrates a prepared cap 500 pre-dosed with an astringent or hemostatic agent. The prepared cap 500 is made of a porous material that is resilient and hydrophilic. The porous material may be made of vinyl acetate and is preferably an ethylene vinyl acetate copolymer. The prepared cap 500 may be made of a fiber, foam, or sintered material. The prepared cap 500 has cylindrical walls 512 with an open end having a bevel 514. The bevel 514 is adapted to aid in applying pressure to the gingival or gum tissue and assist in retraction. The interior 520 is cylindrical and may have a slight taper. The prepared cap 500 is pre-dosed with an astringent or hemostatic agent 519 interspersed in the porous material of the cap 500. A solution is prepared containing a solvent of water or alcohol or other solvent and an astringent or hemostatic agent, such as aluminum sulfate, aluminum ammonium sulfate, aluminum potassium sulfate, aluminum chloride, ferric sulfate, ferric chloride, alum, tannic acid, or other well known astringent or hemostatic agent. The solution preferably comprises between five and thirty-five percent by weight astringent or hemostatic agent.

The prepared cap 500 may also comprise other shapes or forms, such as a multiple of prepared caps for fitting multiple teeth, for example as illustrated in FIG. 17 or an elongated cap with a longitudinal groove as illustrated in FIG. 2 or 7.

FIG. 27 illustrates the method of preparing and using a prepared cap use in retraction. Box 600 represents the step of creating a solution of between five and thirty-five percent by weight of an astringent or hemostatic agent. Box 602 represents the step of saturating a porous cap with the solution. The saturating of the porous cap may be accomplished by dipping the porous cap in the solution, or spraying or pouring the solution on the porous cap. Box 604 represents the step of drying the porous cap forming a prepared cap. The step of drying may be accomplished by air drying or heating in an oven at an elevated temperature, preferably approximately one-hundred and fifty degrees Fahrenheit. Box 606 represents the step of preparing a tooth for restoration. Generally, the restoration may be preparation for a bridge or crown procedure which generally includes the taking of an impression of the area surrounding the prepared tooth. Box 608 represents placing the prepared cap over the prepared tooth. Box 610 represents applying pressure to the prepared cap for between three and five minutes. The pressure may be applied by the patient biting down on the prepared cap. Box 612 represents the step of removing the prepared cap from the prepared tooth.

This embodiment of the invention may be used in combination with other retraction devices or methods. For example, conventional retraction cord may be packed between the tooth and sulcus or gum tissue prior to use of the pre-dosed prepared cap. Additionally, the pre-dosed prepared cap may be filed with a material to aid retraction of the gum tissue prior to placement over the prepared tooth. Therefore, the additional step of applying a retraction material around a prepared tooth may be employed as well as placing the retraction material initially within the prepared cap.

This embodiment of the invention has the advantage of being convenient and easy to use. The pre-dosed prepared cap may have the dry astringent or hemostatic agent reactivated by moisture in the oral cavity. This aids in the control of any fluids that may be present, including the cessation of bleeding. Additionally, the pressure applied and shape of the beveled edges of the pre-dosed prepared cap aid in separating or retracting the gum tissue as well as controlling bleeding.

While the preferred embodiments and methods of the present invention have been shown and described herein, it will be apparent to those skilled in the art that various modifications and variations may be made without departing from the spirit and scope of the invention as claimed herein.

What is claimed is:

1. A pre-dosed prepared cap used in gingival retraction comprising:
    a shaped porous resilient and hydrophilic cap having cylindrical walls with an open end having a bevel; and
    an initially inactive dry astringent or hemostatic agent contained within said shaped porous resilient and hydrophilic cap,
    whereby said initially inactive dry astringent or hemostatic agent is made active upon exposure to moisture.

2. A pre-dosed prepared cap as in claim 1 wherein:
    said initially inactive dry astringent or hemostatic agent is selected from the group consisting of aluminum sulfate, aluminum ammonium sulfate, aluminum potassium sulfate, aluminum chloride, ferric sulfate, ferric chloride, alum, and tannic acid.

3. A pre-dosed prepared cap as in claim 1 wherein:
    said shaped porous resilient and hydrophilic cap is made of a material selected from the group consisting of a fiber, foam, and sintered material.

4. A pre-dosed prepared cap as in claim 1 wherein:
    said shaped porous resilient and hydrophilic cap is made of ethylene vinyl acetate copolymer.

5. A method of retracting the gingival or gum tissue about a prepared tooth to be restored, comprising the steps of:
    positioning a prepared shaped porous resilient and hydrophilic cap having cylindrical walls and an open end pre-dosed with a dry initially inactive astringent or hemostatic material onto a prepared tooth;
    reactivating the initially inactive astringent or hemostatic material with moisture;
    applying a pressure onto the prepared shaped porous resilient and hydrophilic cap for a predetermined time, whereby the prepared shaped porous resilient and hydrophilic cap applies pressure to the gingival or gum tissue and assists in retraction; and
    removing the prepared shaped porous resilient and hydrophilic cap cap from the prepared tooth,
    whereby the gingival tissue is retracted away from the tooth to enlarge the sulcus.

6. A method of retracting the gingival or gum tissue time as in claim 5 wherein:
    the predetermined time is between three and five minutes.

7. A method of retracting the gingival or gum tissue time as in claim 5 further comprising;
    the step of applying a retraction material around the prepared tooth.

8. A method of retracting the gingival or gum tissue time as in claim 7 wherein:
    a retraction material is placed initially within cap.

9. A method of retracting the gingival or gum tissue time as in claim 5 wherein:
    the open end of the prepared shaped porous resilient and hydrophilic cap has a bevel.

* * * * *